United States Patent [19]
Bergman

[11] Patent Number: 5,495,863
[45] Date of Patent: Mar. 5, 1996

[54] FLOSSING DEVICE WITH ADVANCING AND TENSIONING MECHANISMS

[76] Inventor: Mark C. Bergman, 13545 Treasure Way, Chino Hills, Calif. 91709

[21] Appl. No.: 238,389
[22] Filed: May 5, 1994
[51] Int. Cl.⁶ .................................................. A61C 15/00
[52] U.S. Cl. .......................................... 132/326; 132/325
[58] Field of Search ..................................... 132/323, 324, 132/325, 326, 327, 328

[56] References Cited

U.S. PATENT DOCUMENTS

| | | |
|---|---|---|
| 754,841 | 3/1904 | Bessonet . |
| 1,666,877 | 4/1928 | Cummer . |
| 2,098,610 | 11/1937 | Bluhm .................................. 132/325 |
| 2,853,082 | 9/1958 | Nelson .................................. 132/326 |
| 3,327,719 | 6/1967 | Ford ...................................... 132/326 |
| 3,533,420 | 10/1970 | Maloney .............................. 132/325 |
| 3,592,203 | 7/1971 | Johnson ................................. 132/91 |
| 3,746,017 | 7/1973 | Casselman ........................ 132/92 A |
| 3,881,502 | 5/1975 | Bennington ........................... 132/91 |
| 3,908,677 | 9/1975 | Beach .................................... 132/91 |
| 4,005,721 | 2/1977 | Yasumoto .............................. 132/91 |
| 4,008,728 | 2/1977 | Sanchez ............................ 132/92 R |
| 4,151,851 | 5/1979 | Bragg .................................... 132/91 |
| 4,178,947 | 12/1979 | McCourry et al. ............... 132/92 R |
| 4,408,920 | 10/1983 | Walther et al. .................. 132/325 X |
| 4,508,125 | 4/1985 | Loubier ............................ 132/92 R |
| 4,518,000 | 5/1985 | Leverette ......................... 132/92 A |
| 4,660,584 | 4/1987 | Wofford ........................... 132/92 A |
| 4,790,336 | 12/1988 | Kuo ..................................... 132/325 |
| 4,817,642 | 4/1989 | Lipp .................................... 132/324 |
| 4,898,196 | 2/1990 | Eason .................................. 132/327 |
| 5,029,593 | 7/1991 | Huttunen ............................. 132/323 |
| 5,038,806 | 8/1991 | Ewald ................................. 132/325 |
| 5,046,212 | 9/1991 | O'Conke ......................... 132/328 X |
| 5,060,681 | 10/1991 | Westbrook et al. ............... 132/325 |
| 5,085,236 | 2/1992 | Odneal et al. ..................... 132/325 |
| 5,105,840 | 4/1992 | Giacopuzzi ........................ 132/325 |
| 5,269,331 | 12/1993 | Tanriverdi ......................... 132/325 |
| 5,375,614 | 12/1994 | Navratil ............................ 132/325 |

FOREIGN PATENT DOCUMENTS

| | | |
|---|---|---|
| 2345137 | 10/1977 | France ............................... 132/323 |
| 2141935 | 1/1985 | United Kingdom . |
| 9107143 | 5/1991 | WIPO ................................ 132/324 |

Primary Examiner—John G. Weiss
Attorney, Agent, or Firm—Christie, Parker & Hale

[57] ABSTRACT

A hand-held dental flossing device has a housing with a handle which may be held with one hand. A dental floss supply is located in the housing and a winding gear is rotatably mounted to the housing. A free end of the dental floss strand from the floss supply is threaded through the housing into a flossing arm of the housing where it passes an opening and returns into the housing to be attached to the winding gear. The housing has an opening where the winding gear extends therefrom and is accessible to the fingers of the user's hand. The winding gear has teeth which cooperate with a stopper to form a one-way ratchet gear. A floss tensioning button is located in the housing and has first and second ends extending from the housing. The first and second ends are accessible to the user's hand holding the handle of the flossing device. When in a first position, the tensioning button allows the floss strand to be readily advanced by winding the gear while in a second position, the floss strand is relatively taut so that winding the gear will even further tension the strand.

19 Claims, 6 Drawing Sheets

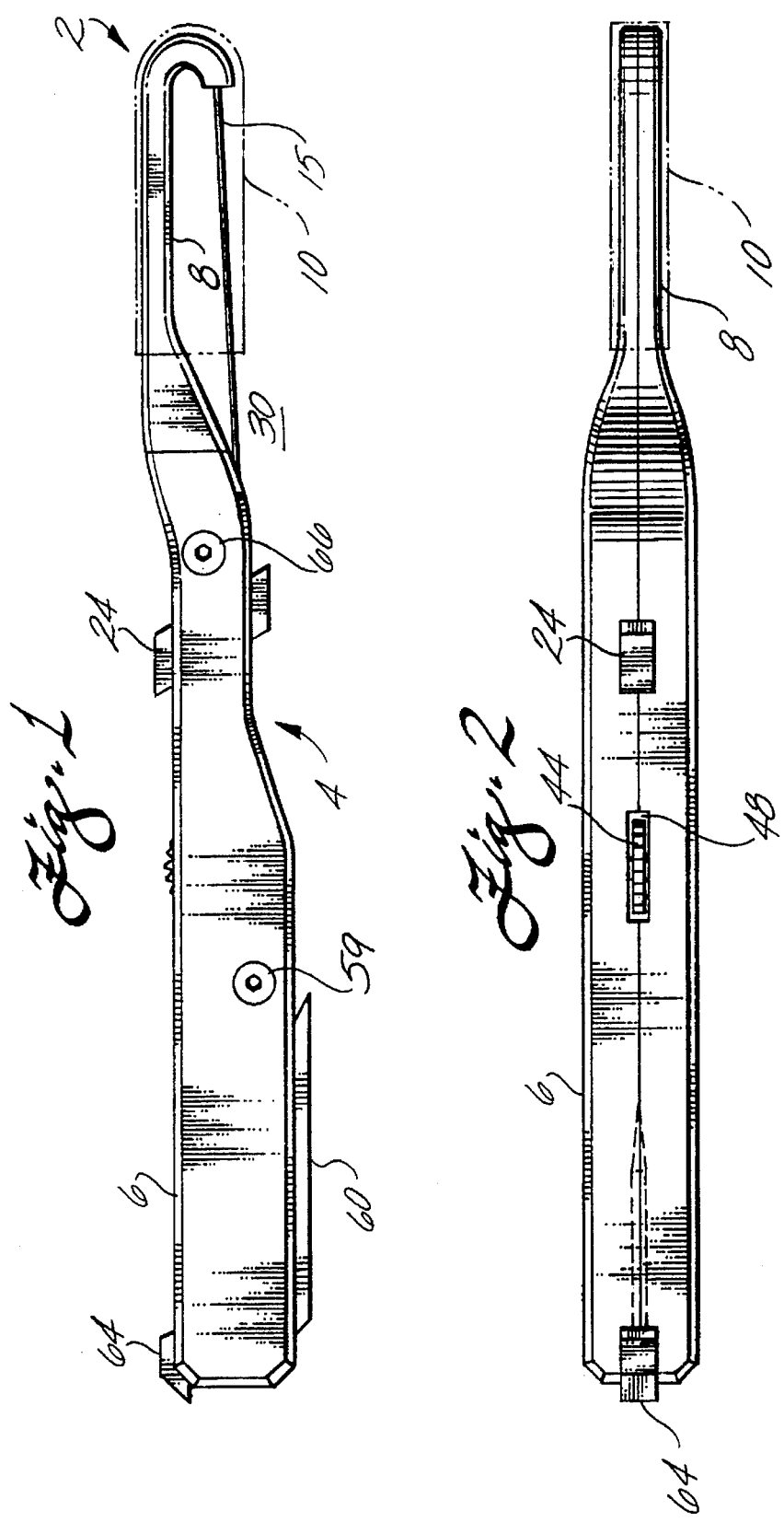

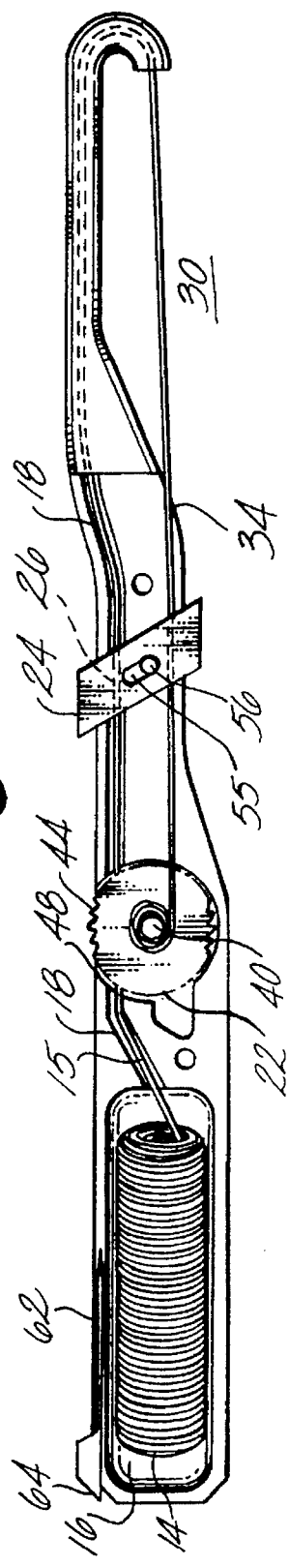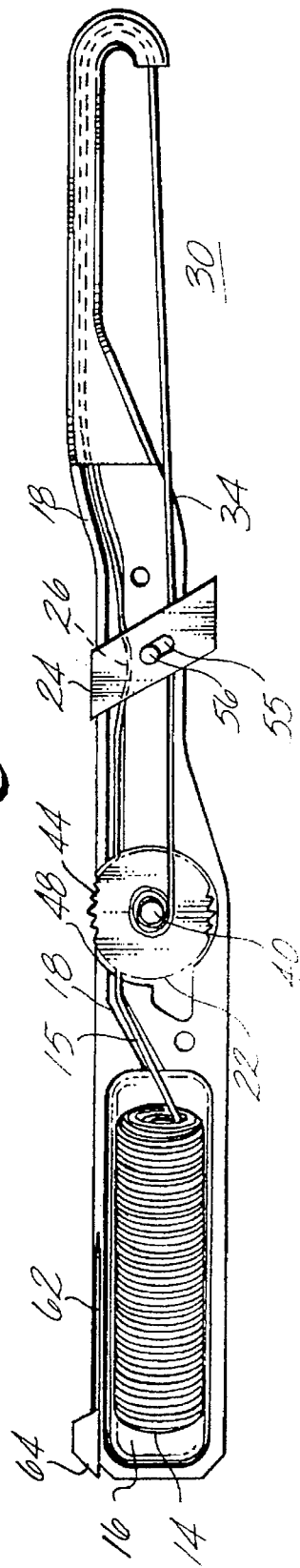

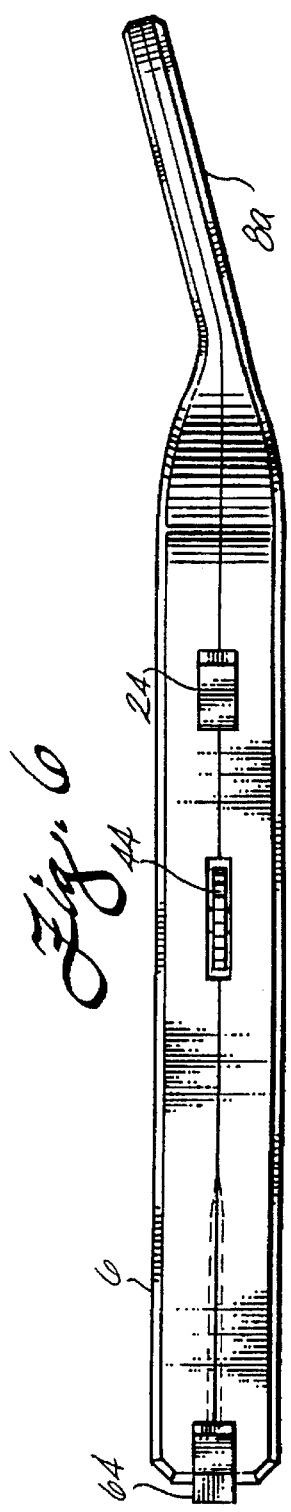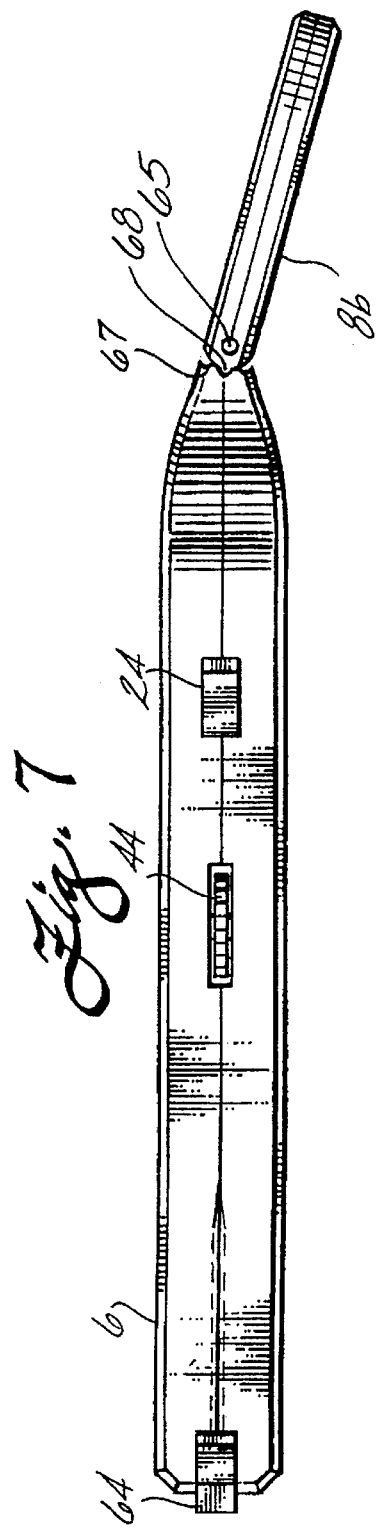

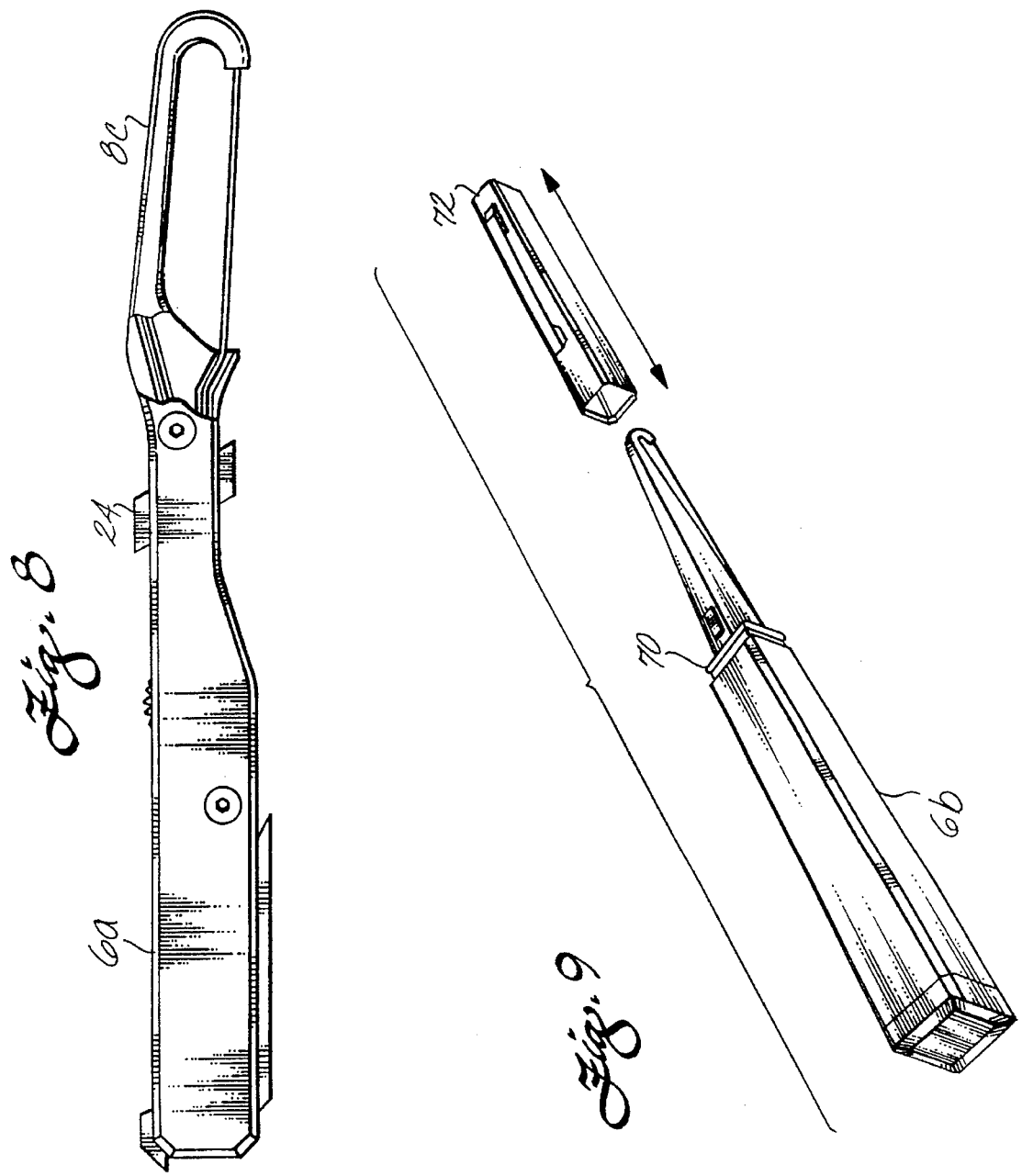

FLOSSING DEVICE WITH ADVANCING AND TENSIONING MECHANISMS

FIELD OF THE INVENTION

The present invention relates to a hand-held flossing device, which has a floss advancing mechanism and a simple-to-use tensioning mechanism for providing the floss with sufficient tension to be of practical use.

BACKGROUND OF THE INVENTION

Flossing regularly is important to dental health. However, flossing by holding the floss tightly between the user's two hands is cumbersome because it is hard to reach back teeth, and it is often hard to achieve sufficient tension without hurting one's hands. Moreover, it is not a sterile practice because the user's hands touch both fresh and used floss.

To simplify flossing and avoid some of these problems, many flossing aids have been developed. In fact, an early flossing device is disclosed in U.S. Pat. No. 754,851 issued Mar. 15, 1904 to Bessonet, which provides for a manually threaded fork and a tensioning screw to tighten the floss when threaded. Because in this device the floss must be manually advanced and threaded, its use is cumbersome.

Another flosser is disclosed in U.S. Pat. No. 1,666,877 to Cummer, which issued in 1928. Cummer notes that floss holders have the problem of maintaining the floss taut as it can stretch during use. He uses a spring-loaded actuator arm to try to solve the problem.

U.S. Pat. No. 3,746,017 to Casselman, issued in 1973, discloses a floss holder which includes a floss take-up reel for used floss. A new floss spool is insertable into and a used spool is removable from the device by means of a removable cover which provides access to the spools. New floss is pulled from the supply spool, threaded through the device and wrapped onto a take-up reel. A slide 11 is movable to a position where the supply reel can rotate freely so that floss can be advanced by rotating the take-up reel with the user's fingers. The slide is then moved to a position where the supply reel is locked in place and tension on the floss may be increased by further rotating the take-up reel, due to a spring ratchet system. A problem with this system is maintaining tension. In addition, new floss must be threaded onto or separately provided on a supply reel.

U.S. Pat. No. 5,060,681 to Westbrook, et al. discloses a flosser that includes a take-up reel actuated to advance floss by a user pressing forward and downwardly on an actuator knob which has notches that engage and advance the take-up reel. To lock the reel, the user lets go of the knob which then retracts upwardly and rearwardly due to a spring bias, and locks the reel into place. The device is difficult to enhance the tension on the floss after the user release the knob.

Yet another flosser is disclosed in U.S. Pat. No. 5,269,331 to Tanriverdi issued in 1993. It has supply and take-up reels, the floss being advanced by manually advancing the take-up reel. A locking member prevents any rotation of the supply reel independent of the take-up reel. The take-up reel is rotated to feed new floss by manual advancement. Tension may be provided by pressing and holding down a bulged portion of the case where the supply reel is located.

Other flosser devices are disclosed in the following U.S. Pat. Nos.: 4,790,336; 5,038,806; 5,105,840; 4,660,584; 4,898,196; 5,029,593; 4,005,721; 4,817,642; 3,881,502; 3,592,203; 4,518,000; 4,151,851; 4,178,947; 4,008,728; 3,908,677; and 4,508,152.

What is needed is a flossing device that is simple to use in that it is easy to advance floss and easy to provide enhanced tension to enable one to floss. What is also needed is a flossing device which is easy to hold, safe to use, separates the new and used floss, is easy to manufacture and is compact.

SUMMARY OF THE INVENTION

In one embodiment, the present invention provides a hand-held flossing device including a housing, preferably of plastic, which is generally toothbrush-shaped. The housing has a compartment for new floss and a separate area for used floss. A winding reel is rotatably attached to the housing and the free end of the floss is attached to the reel so that when the wheel is rotated, the floss will unwind from the new floss spool. Used floss will wrap around the winding reel. The reel preferably extends outside the housing so that it can be advanced by the thumb or fingers of the user to advance the floss. A one-way catch allows the serrated winding reel to ratchet. The housing has a handle area and an extending arm from the handle area. A tension knob or trigger is located in the housing. New floss passes from the spool through the tension trigger, through the extending arm and past an open area where the floss is exposed. The floss then returns into the housing and attaches to the winding reel. The floss is advanced by winding the reel. The ratchet action of the reel with the one-way catch prevents loosening of the floss. To tension the floss even more, the tension knob is pressed which pinches the floss to inhibit new floss from being pulled from the spool and also enhances the tension. Further tension may be applied to the floss by winding the take-up reel even more.

In a preferred embodiment, the knob is compression fit or friction fit into the housing and has a slot through which a pin connected to the housing passes. The handle is tapered and the housing is pen or pocket-size. A new floss spool does not require a supply reel. The extension arm is J-shaped rather than having a V-shaped prong to provide a safer, dull arm. The floss in the supply spool is round, oval, or eccentric, and is internally wound which facilitates operation of the invention. The device has a pocket clip and a toothpick or a plaque pick is removably inserted into the device housing for convenience. The device may be provided with a cover which fits over the tapered housing at the J-shaped extension to improve appearance and to provide protection for the exposed portion of the floss during storage. The device may be disposable or nondisposable with the new spool compartment of the device being openable to insert another spool and the winding reel being accessible to attach the end of the new spool.

The device is easy to hold. The simplicity of construction of the device and the ability to easily enhance tension promotes use of the device to stop tooth decay. In fact, the device is constructed so that it is easy for all to use regardless of age or ability, including the elderly who may have arthritis or the very young who may lack coordination. Moreover, the device maintains separate sections for new and used floss to help prevent the spread of germs and thus is quite useful for those with gum and mouth diseases and may even have application with HIV-positive persons.

BRIEF DESCRIPTION OF THE DRAWINGS

These and other advantages, features and aspects of the preferred embodiment of the invention may be more apparent with reference to the detailed description to be read in conjunction with the drawings, in which:

FIG. 1 is a side view of a first embodiment of a flosser according to the invention;

Figure 5:
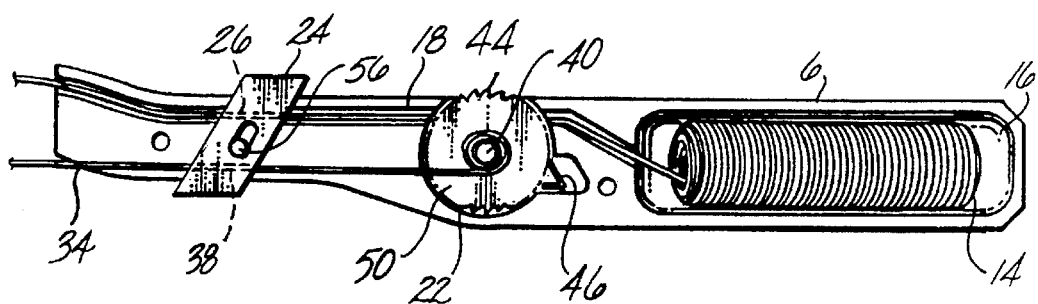
Figure 10:
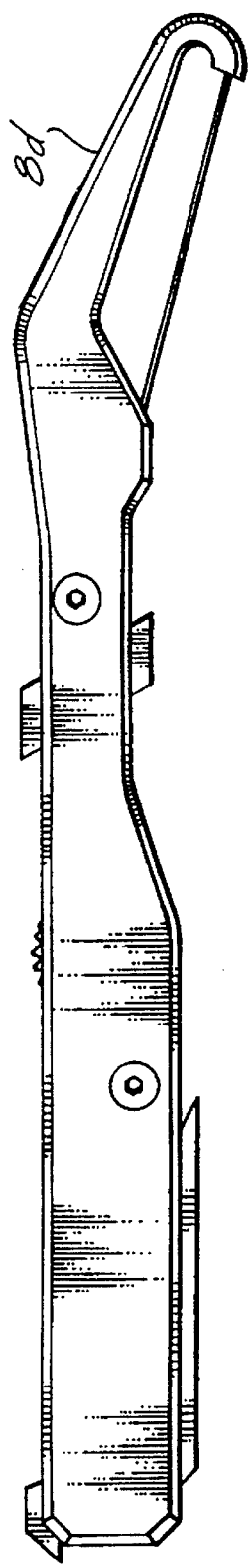
Figure 11:
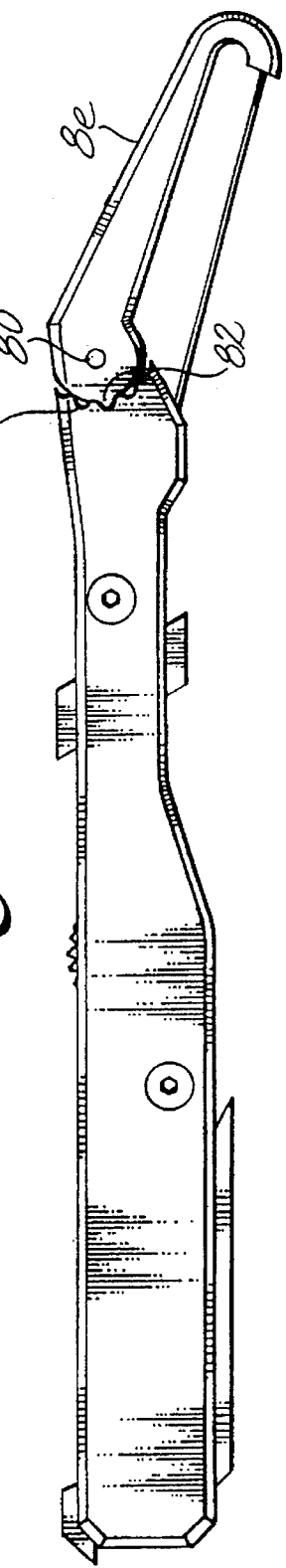

JIG. 2 is a top view of the flosser of FIG. 1 with its cover on;

FIG. 3 is a side view of the flosser with its side open to show internal components;

FIG. 4 is a view similar to FIG. 3 with a tensioning knob in the actuated position;

FIG. 5 is a partial view of the other side of the flosser with its side open to show the other side of the internal components;

FIG. 6 is a top view of a flosser having a flossing arm bent to the left when looking down according to a second embodiment of the invention;

FIG. 7 is a top view of a flosser having a flossing arm bent to the right when looking down according to a third embodiment of the invention and in which the flossing arm is pivotable left and right;

FIG. 8 is a side view of a flosser bent downward according to a fourth embodiment of the invention;

FIG. 9 is an exploded perspective view of a flosser according to a fifth embodiment of the invention;

FIG. 10 is a side view of a sixth embodiment of the invention, where the arm is bent downward; and FIG. 11 is a side view of a seventh embodiment of the invention where the arm is pivotable up and down.

DETAILED DESCRIPTION OF THE PREFERRED EMBODIMENT

In general, a flossing device according to the invention in a preferred embodiment has an easy-to-use tensioning or locking button to increase the tension on the floss. In one embodiment of the invention, as shown in FIGS. 1–5, a flosser 2 has a generally elongated housing 4 including a handle 6 and a flossing arm 8. Preferably, the device is shaped so that it may be held like a toothbrush. There is a cover 10 which is fit over the flossing arm 8 and may be held thereon by a friction fit.

A spool 14 of floss 15 fits in a compartment 16 of the flosser. The floss spool is preferably round, oval, or eccentric and is internally wound. An eccentric shape, such as substantially rectangular, allows one to maximize the amount of floss supply to fit whatever design and shape exists for compartment 16 which, in turn, may be dictated by the handle design and shape. Internal winding enables the free end of the floss to be at the inside of the spool so that a winding reel is not needed, although one could be used where externally winding the floss is desired.

The floss passes out of compartment 16 through a channel 18 past one side of a winding gear 22 and on through a tensioning button 24 having an aperture 26 through which the floss passes. The floss continues on through channel 18 into the flossing arm 8, which preferably has a J-shape (and/or bent J-shape or pivotable J-shape). The floss 15 exits the J-shape to an exposed area 30 and returns into the housing at an opening 34 and passes through tensioning button 24 at an aperture 38. The floss then passes to the winding gear 22 where it is fixed to an axle 40 on an opposite side of the gear as the floss when coming from spool 14. The axle 40 is fixed to the gear so that rotation of the gear rotates the axle to wind the floss around the axle and at the same time advance floss from spool 14. Gear 22 has serrations 44 on its periphery which mesh with a ratchet arm 46 (FIG. 5), such as a spring clip. The ratchet arm and serrations cooperate so that the winding gear rotates only in one direction to pull floss from spool 14. The winding gear may be advanced by a user holding handle 6 by pulling or pushing on an exposed portion of winding gear 22 proximate an opening 48 in the top of the housing. Whether the gear will be pulled or pushed depends on which way the serrations and ratchet allow the gear to be wound. The portion of the floss wound on axle 40 is isolated in another compartment 50 on the side of the gear 22 where the floss attached to axle 40. The axle 40 is rotatable with respect to the housing.

In the past, it has been difficult to achieve sufficient tension on the floss to perform flossing. Even where sufficient tension could be obtained, the mechanism to obtain it would be quite complex. In the invention, the single tensioning button 24 is used. It is preferably press fit into a channel in the housing and is normally kept in a first, low tension position (e.g., FIG. 3) where the floss in channel 18 and the return floss pass substantially straight through the button. After the user winds the floss to obtain fresh floss in the exposed area 30, the fresh floss may be further tensioned by pressing button 24 so that the floss passing though the button 24 becomes out of alignment with the floss in channel 18 to lengthen the path of the floss and mainly to pinch it between the button and the housing, and thereby enhance the tension thereon. (A horizontally slidable tensioning button which uses the same type of pinching action may be used in place of a vertically movable button.) This pinching also inhibits advancing the floss from spool 14. Accordingly, to further enhance the tension, the winding gear 22 may be further wound which will tighten the floss from the nearest point, i.e., where it exits the aperture 26 of the tension button 24 to the point where it attaches to axle 40.

The floss supply spool is, in effect, locked off by the tension button pinching the floss between it and the housing. The floss which returns through button 24 to axle 40 passes through a wide channel or no channel such that it will not be pinched by movement of the button. Accordingly, the tension of the floss in the exposed area 30 is further enhanced by ratchet action. The user then flosses until the exposed floss is spent. Then the user may further advance the floss by moving the tensioning button back to the first position and by further winding gear 22. The user will then move the tensioning button back to the second position and enhance the tension as needed for additional flossing. As can be seen from the drawings, the operation of holding the flosser 2, advancing the floss using winding gear 22 and further tensioning the floss using the tension button 24 can all be performed with one hand. The tension button 24 can be pushed from the top or bottom of the flossing device and so it is very simple to tension or release the floss.

As shown in FIGS. 1–5, tensioning button 24 has an elongated hole 55 through which a pin 56 fixed to the housing 4 passes. The pin defines the limits of motion of the tensioning button so that the button will stay connected to the housing and so that the first and second positions of the button are defined.

The underside of handle 6 of the housing can have a pocket clip 60 attached to it similar to a pocket clip on a pen. The housing may also have a slot 62 defined in it for receiving a plaque pick 64 similar to a plaque or toothpick in a pocket knife.

Housing 4 is preferably injection-molded in left and right halves. The halves may be fixed together by known means, such as screws 59, 66, glue, or epoxy. The flosser may be constructed to be disposable when the floss is used up or in such a way that the floss compartment 16 can be exposed and the rest of the floss path so that the old floss can be removed and a new floss spool can be inserted in the compartment with sufficient floss to be threaded to the rest of the device and attached to axle 40 at its free end, e.g., by means of a monofilament leader at the free end.

The handle preferably tapers so that the handle can be sufficiently thick to readily hold while the extending arm or flossing arm is sufficiently thin to be easy to maneuver within the user's mouth. A J-shaped or hook-shaped flossing arm instead of two prongs avoids sharp, exposed edges and is also easier to use in that the device may be held and used like a toothbrush.

Alternative embodiments are shown in FIGS. 5–10 as follows:

FIG. 6 is the top view of a flosser substantially the same as the flosser of FIGS. 1–5, except that the extension or flossing arm 8a is bent to the left, and FIG. 7 is the same as the flosser of FIGS. 1–5, except that the flossing arm 8b is bent to the right. These embodiments may be easier for certain people to use to get at molars or wisdom teeth. This arm 8b is pivotable left and right about a pin 65 (internally connected to handle 6), and is held at a desired angle by a detent mechanism, including detent surface 67 of the handle and a projection 68 of the arm 8b.

The embodiment of FIG. 8 is also the same as that of FIGS. 1–5, but it has a handle 6a and slight downward bend of the flossing arm 8c, which may make it easier for some users to reach different teeth. For the embodiment of FIG. 8, a suitable cover can be designed. Obviously, any embodiment may be made with a suitable cover.

The embodiment of FIG. 9 shows a pocket-size version of the device which has the same components as that of FIGS. 1–5, but has a handle 6b and a square-shaped cross section and has a detent mechanism 70 to hold its cover 72. There may also be a plaque pick and clip in this version. The spool in this version is longer and narrower, similar to the models shown in FIGS. 10 and 11. However, the differences between the model of FIGS. 10 and 11 are that FIG. 10 has a substantially angled flossing arm 8d, while FIG. 11 has an up and down, pivotable flossing arm 8e. The flossing arm of FIG. 11 is journaled to the rest of the housing about a pivot pin 80 and is held in place at the selected angle by means of tension detents 84 on the handle and a projection 82 on the arm similar to the side-to-side pivotable system of FIG. 7.

Modifications and improvements of the present invention will be apparent to those skilled in the art. For example, the tensioning button may have first and second ends protruding from the sides of the housing rather than the top and the bottom of the housing. The invention is not limited to the disclosed embodiments but is defined by the appended claims.

I claim:

1. A hand-held dental flossing device, comprising:
   (a) a housing having a handle and a flossing arm and a top and a bottom;
   (b) a dental floss supply disposed in the housing;
   (c) a winding gear rotatably mounted to the housing for having a free end of a dental floss strand from the supply attached to the gear, the winding gear having a portion extending through the top of the housing proximate the handle;
   (d) a floss tensioning button mounted in the housing and having floss passing from the supply past the button to the flossing arm and returning to the winding gear, the button being movable from a floss threading position where the floss strand is relatively loose so that it may be wound by the winding gear to a floss locking position where the floss strand is locked by friction fit between the button and the housing so that the floss is relatively tight and where, in response to further winding of the winding gear with the button in the floss locking position, the floss strand will be further tensioned between the button and the winding gear, wherein the button has a first end extending from the top of the housing at a location closer to the flossing arm than the winding gear is to the flossing arm, whereby a user of the device can wind the floss and press the first end of the button using a hand which is holding the handle.

2. The flossing device of claim 1, wherein the floss tensioning button has at the bottom of the housing directly below the first end so that a user can actuate the second end of the button with the same hand that holds the handle.

3. The flossing device of claim 1, further comprising a pocket clip attached to the housing.

4. The flossing device of claim 1, further comprising a plaque pick attached to the housing.

5. The flossing device of claim 1 wherein the housing tapers from the handle to the flossing arm.

6. The flossing device of claim 1 wherein the floss supply is eccentrically, internally wound.

7. The flossing device of claim 1 wherein the flossing arm has a J-shape.

8. The flossing device of claim 1 wherein the flossing arm is bent to one side or the other with respect to the handle of the housing.

9. The flossing device of claim 1 wherein the flossing arm is pivotable with respect to the handle of the housing.

10. The flossing device of claim 1 further comprising a removable cap fitting over the flossing arm.

11. The flossing device of claim 1 wherein the housing has a used floss compartment defined therein on the side of the winding gear where the free end of the floss strand is attached, the used floss compartment being separated from the compartment in which the floss supply is disposed.

12. The flossing device of claim 1 further comprising a stopper fixed to the housing for cooperating with the winding gear to limit the winding gear to one-way rotation.

13. The flossing device of claim 12 wherein the winding gear has serrations which cooperate with the stopper to provide a ratchet mechanism.

14. The flossing device of claim 1 wherein the housing has a channel defined therein for the floss strand so that the floss strand will be pinched between the channel and the tensioning button.

15. The flossing device of claim 1 wherein the button has an aperture formed therein and the floss passes through the aperture.

16. A hand-held dental flossing device, comprising:
   (a) a housing;
   (b) a dental floss supply disposed in the housing;
   (c) a winding gear rotatably mounted to the housing for having a free end of a dental floss strand from the supply attached to the gear;
   (d) a dental floss path formed in the housing from the supply to pass an opening in a flossing arm of the housing where the floss strand is exposed; and
   (e) a floss tensioning button mounted in the housing and having first and second opposite ends, wherein each end extends away from the each for extending from the housing in response to pressing on the other end, the first end being actuable by pressing to move the button from a floss threading position where the floss strand is relatively loose so that it may be wound by the winding gear to a floss locking position where the floss strand is relatively tight by friction fit of the floss between the button and housing so that winding the winding gear will further tension the floss strand and the second end being actuable by pressing to move the button from the floss locking position to the floss threading position.

17. The flossing device of claim 16, wherein the winding gear extends from the housing proximate-the handle so that a user can actuate the winding gear with the same hand that holds the handle.

18. The flossing device of claim 16 wherein the button has an aperture formed therein and the floss passes through the aperture.

19. The flossing device of claim 16 wherein the button is friction fit in the housing.

* * * * *